(12) United States Patent
Yoon et al.

(10) Patent No.: US 8,616,703 B2
(45) Date of Patent: Dec. 31, 2013

(54) MEASURING OCULAR POINT SPREAD FUNCTION USING ADAPTIVE OPTICS

(75) Inventors: Geunyoung Yoon, Pittsford, NY (US); Ramkumar Sabesan, Rochester, NY (US)

(73) Assignee: University of Rochester, Rochester, NY (US)

(*) Notice: Subject to any disclaimer, the term of this patent is extended or adjusted under 35 U.S.C. 154(b) by 106 days.

(21) Appl. No.: 13/297,554

(22) Filed: Nov. 16, 2011

(65) Prior Publication Data

US 2012/0127432 A1    May 24, 2012

Related U.S. Application Data

(60) Provisional application No. 61/414,281, filed on Nov. 16, 2010.

(51) Int. Cl.
*A61B 3/10* (2006.01)
*A61B 3/00* (2006.01)

(52) U.S. Cl.
USPC .......................................... 351/221; 351/246

(58) Field of Classification Search
USPC .................................................. 351/200–246
See application file for complete search history.

(56) References Cited

U.S. PATENT DOCUMENTS

| | | | |
|---|---|---|---|
| 2003/0151721 A1* | 8/2003 | Lai et al. | 351/212 |
| 2005/0174535 A1* | 8/2005 | Lai et al. | 351/205 |

\* cited by examiner

*Primary Examiner* — Mohammed Hasan
(74) *Attorney, Agent, or Firm* — Blank Rome LLP

(57) ABSTRACT

Measurement of the optical point spread function through a double-pass technique is enhanced by using adaptive optics to form a tiny spot of light on the retina.

11 Claims, 21 Drawing Sheets

*The PSF is the image that an optical system forms of a point source.*

- Diffraction
- Aberrations
- Scatter $$PSF(x, y) \otimes O(x, y) = I(x, y)$$

MEASURING OCULAR POINT SPREAD FUNCTION USING ADAPTIVE OPTICS

REFERENCE TO RELATED APPLICATION

The present application claims the benefit of U.S. Provisional Patent Application No. 61/414,281, filed Nov. 16, 2011, whose disclosure is hereby incorporated by reference in its entirety into the present disclosure.

FIELD OF THE INVENTION

The present invention is directed to a technique for measuring the ocular point spread function, particularly using a technique in which adaptive optics is used to form a tiny point source on the retina after correcting ocular higher order aberrations.

DESCRIPTION OF RELATED ART

The point spread function (PSF) is a comprehensive measure of the eye's ability to form images and is based on the diffraction, aberration, and scatter from the ocular components. Given a perfect object $O(x,y)$, an eye with a point spread function $PSF(x,y)$ will form an image $I(x,y)=PSF(x,y) \otimes O(x,y)$ where $\otimes$ indicates convolution. This is illustrated in FIG. 1.

Our understanding of the optical quality of the eye is becoming more accurate with the ability to precisely measure the lower and higher order wave aberrations using ocular wavefront sensing techniques. Reliable measurements of the ocular wave aberration also make it possible to correct these aberrations to improve visual performance using advanced methods such as adaptive optics, laser refractive surgery, and customized optics. Once the wavefront aberration is measured, the PSF and the corresponding optical transfer function can be theoretically estimated to study the image forming properties of the eye.

Shack-Hartmann ocular wavefront sensors have been the most popular in the field of ophthalmology and vision science. Although they have been used widely, their lateral resolution is limited by the finite sampling of the wavefront by the Shack-Hartmann lenslet array. Since each lenslet averages a distorted wavefront within the lenslet, the highest measurable resolution and spatial frequency in wavefront is limited by size of the lenslet. Therefore, it is limited in applications such as measuring tear film dynamics (dry eye) and scatter (cataract), where it is critical to measure very high spatial frequency wavefronts to accurately assess the optical quality of the eye.

Double pass techniques of measuring the optical transfer function of the eye have been previously employed. The basic symmetric double-pass inherently leads to the loss of odd-aberrations and phase information in the optical transfer function by imparting the same aberration in both passes as shown in FIG. 2. In this way, only the modulation transfer of the eye can be estimated. The asymmetric double pass filters the higher spatial frequency features in the PSF due to an extended laser beacon on the retina induced by a small pupil in the first pass (FIG. 3). The traditional double-pass techniques therefore do not adequately capture the ocular PSF completely.

SUMMARY OF THE INVENTION

It is therefore an object of the invention to measure completely the optical quality of the eye, specifically the very high spatial frequency wavefront aberrations. It is another object of the invention to do so while avoiding the above-noted issues in the prior art, specifically loss of phase information and high spatial frequency features in PSF.

To achieve the above and other objects, the present invention is directed to a technique for measuring the PSF of the eye by creating a tiny point source on the retina using adaptive optics (AO). For example, wavefront aberrations could be measured with a large pupil first, using any suitable wavefront sensor. Then, the wavefront aberrations could be used during an asymmetric AO double-pass technique so that during the first pass with a large pupil, AO could counteract the aberrations to focus the light to form a tiny spot on the retina. In the second pass with a large pupil, the spot scattered from the retina undertakes the entire optical defects of the eye and forms the ocular PSF. The PSF can then be Fourier transformed to obtain the entire optical transfer function including the intensity modulation transfer and phase transfer functions.

BRIEF DESCRIPTION OF THE DRAWINGS

A preferred embodiment of the invention will be set forth in detail with reference to the drawings, in which.

DETAILED DESCRIPTION OF THE PREFERRED EMBODIMENT

A preferred embodiment of the invention will be set forth in detail with reference to the drawings.

Figure 1:
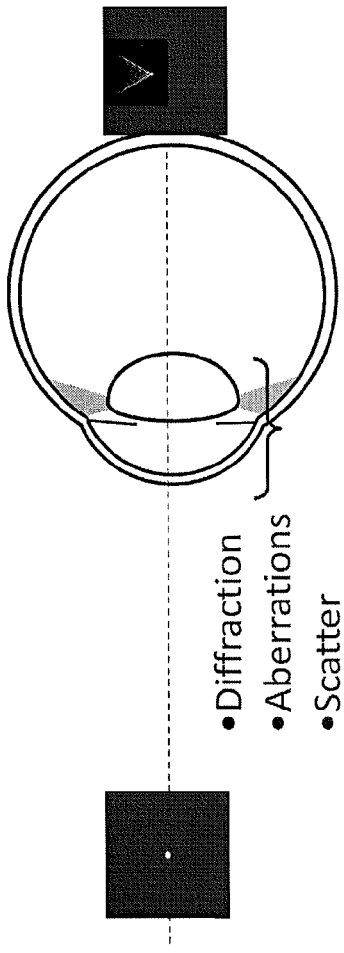
FIG. 1 is a diagram that shows the way in which the PSF affects vision.
Figure 1:
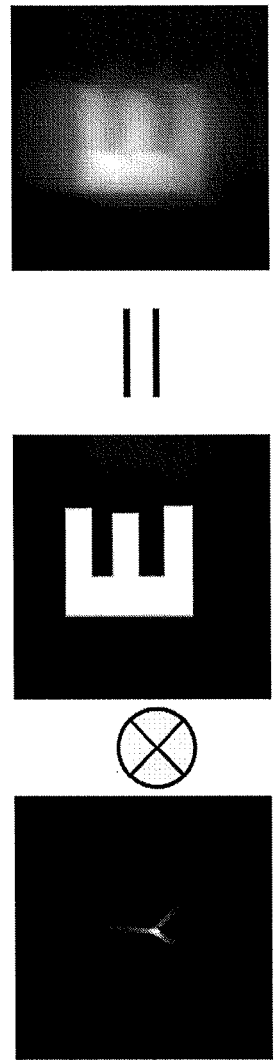
Figure 2:
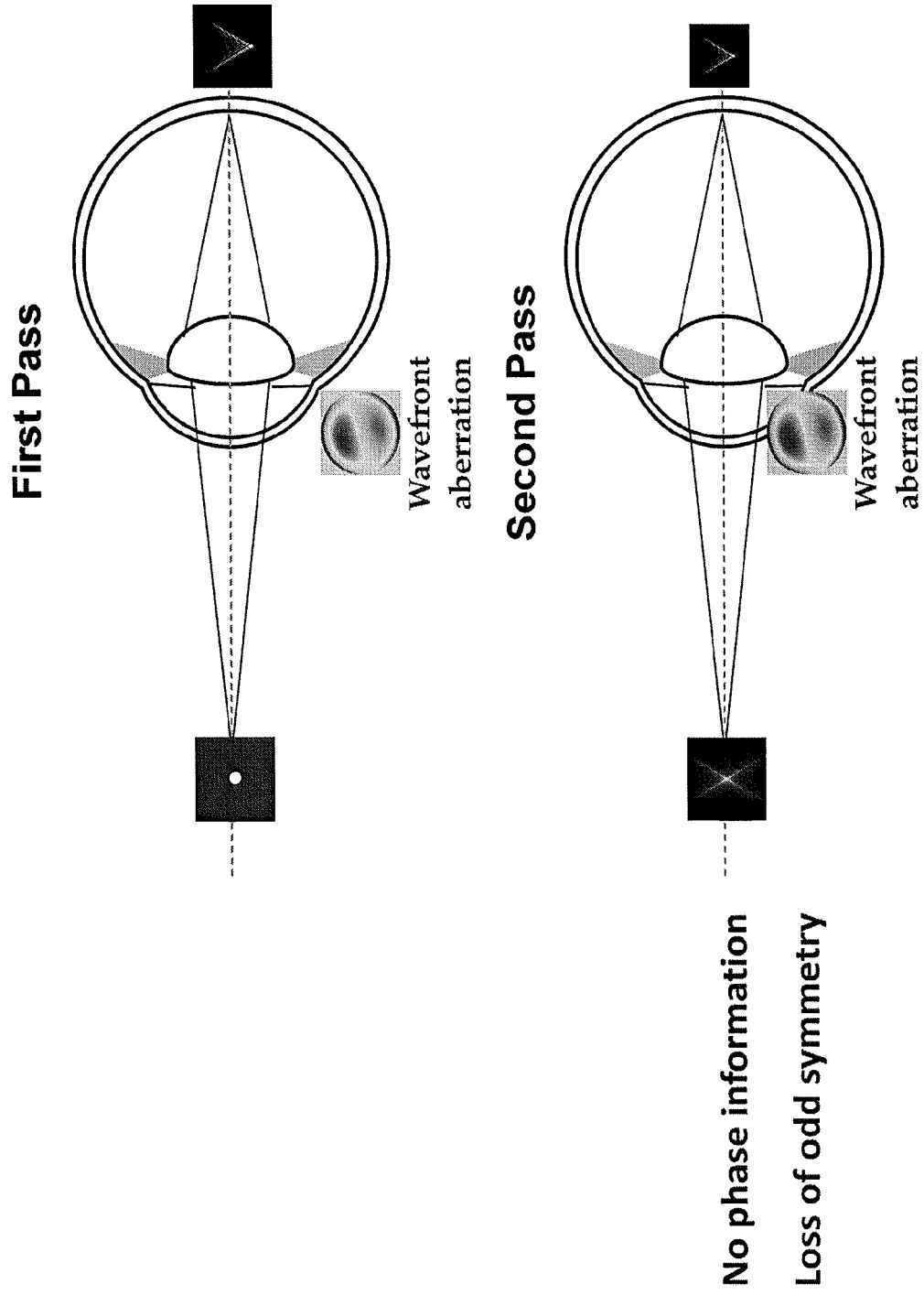
FIG. 2 is a diagram that shows the basic symmetric double-pass technique.
Figure 3:
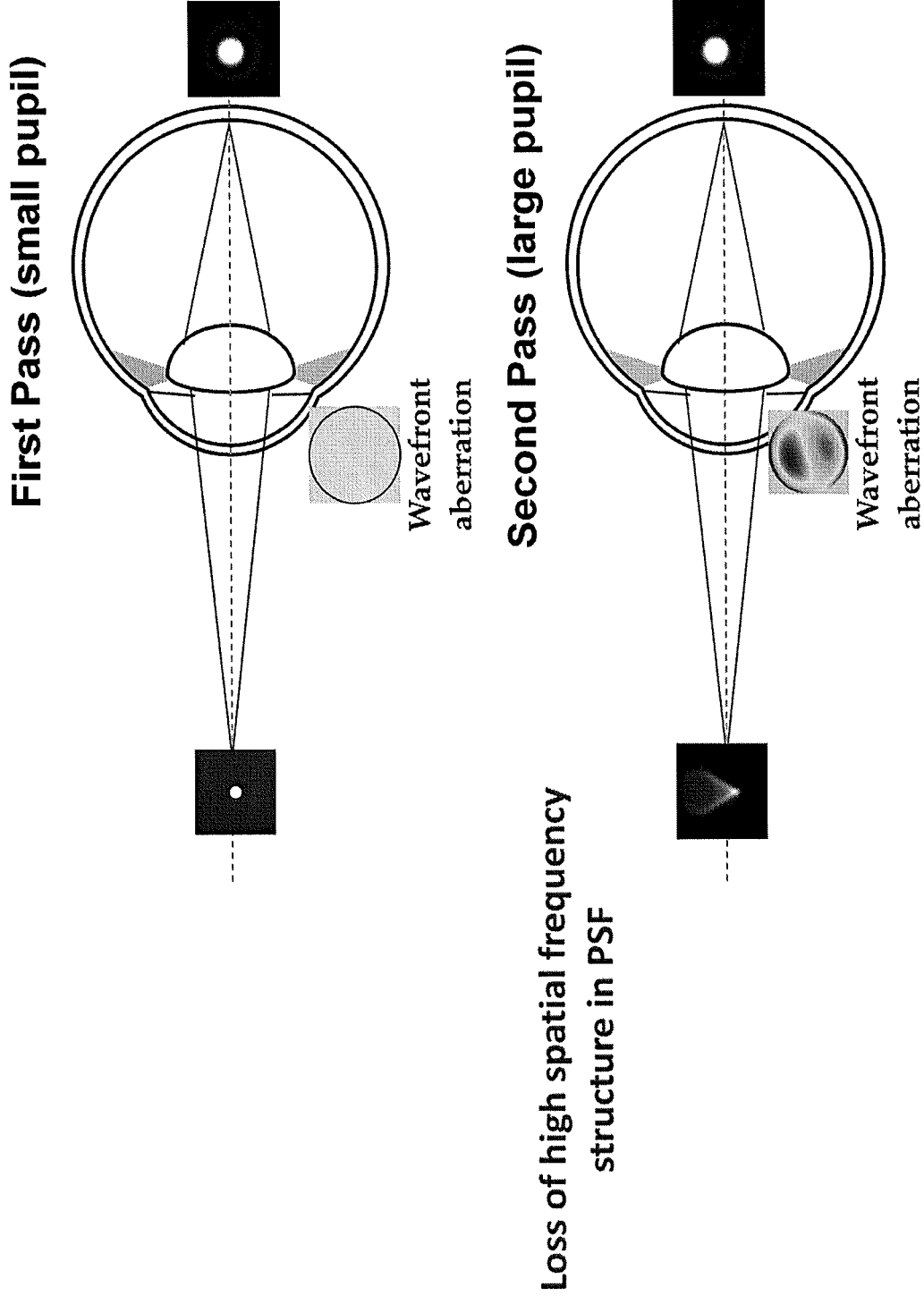
FIG. 3 is a diagram that shows the asymmetric double-pass technique.
Figure 4:
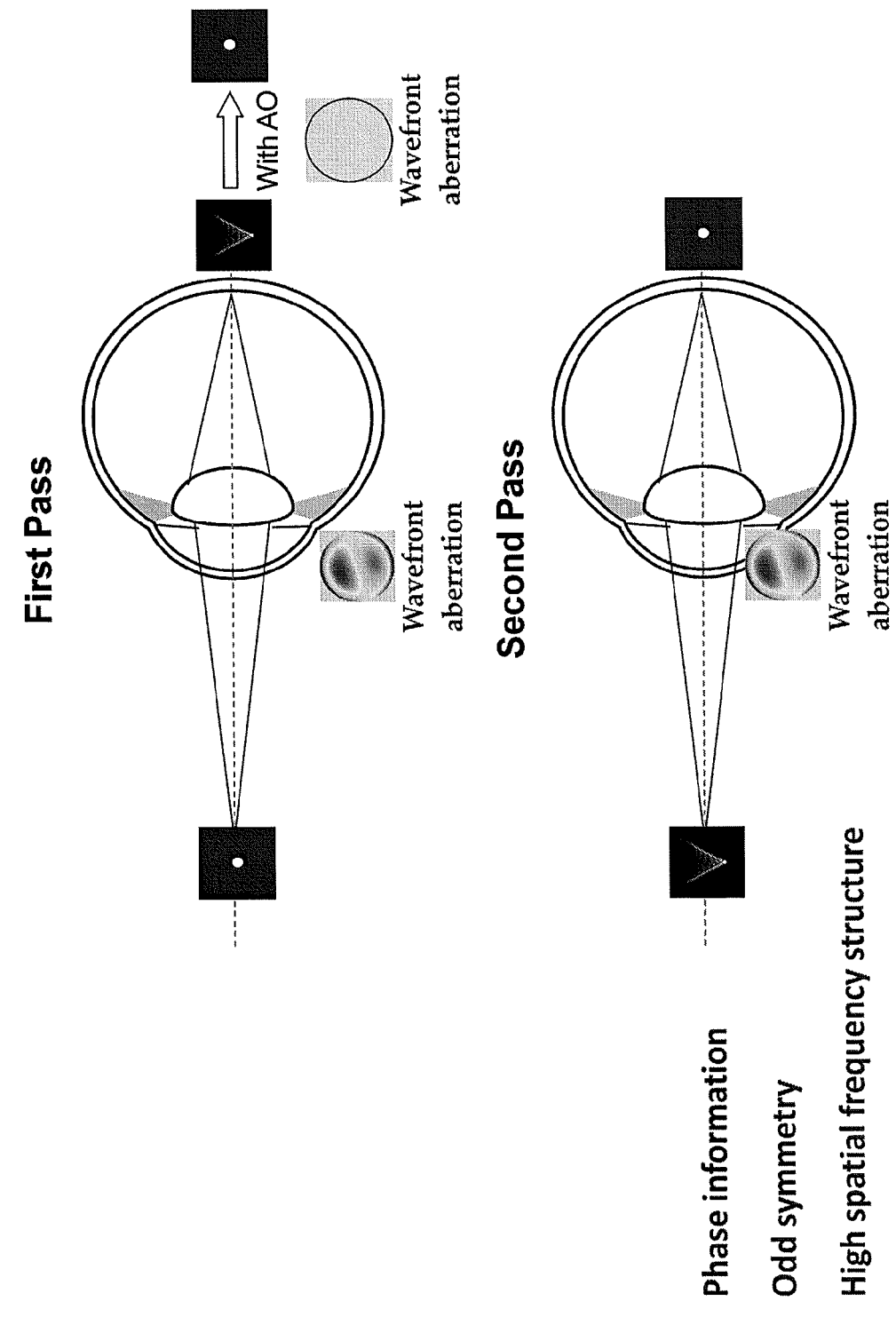
FIG. 4 is a diagram that shows the adaptive optics asymmetric double-pass technique.

FIG. 4 shows an adaptive optics (AO) asymmetric double-pass technique, which overcomes the limitations of the traditional symmetric and asymmetric double-pass techniques in the following respects. In the first pass with a large pupil, wavefront aberrations are removed by using adaptive optics to form a tiny spot on the retina. In the second pass again with a large pupil, light scattered from the retinal point captures the entire optical characteristics of the eye, including the phase information, odd symmetry, and high spatial frequency structure, to form the ocular PSF. Any suitable technique for measuring the wavefront aberrations, such as the use of the above-mentioned Shack-Hartmann detector, as well as any suitable adaptive optics, such as a deformable mirror, can be used. Such matters are known in the art, although the methodology of their use in the present invention is deemed to be novel. Once the PSF is known, it can be used to provide a comprehensive understanding of the image forming properties of the eye. Additionally, this information can be used to design and develop vision corrective devices, e.g., by generating a prescription or by controlling a custom lens fabricator.

The aforementioned method can be refined to measure PSFs due to selective or partial optical effects. By placing a lower-order prescription in the pupil plane in the second pass, the optical PSF attributed to only higher order aberrations, scatter and high spatial frequency defects can be measured. By correcting aberrations completely, partially or selectively in second pass also with a large pupil, the optical PSF attributed to particular aberrations, scatter and high spatial frequencies can be measured and separated.

Figure 5:
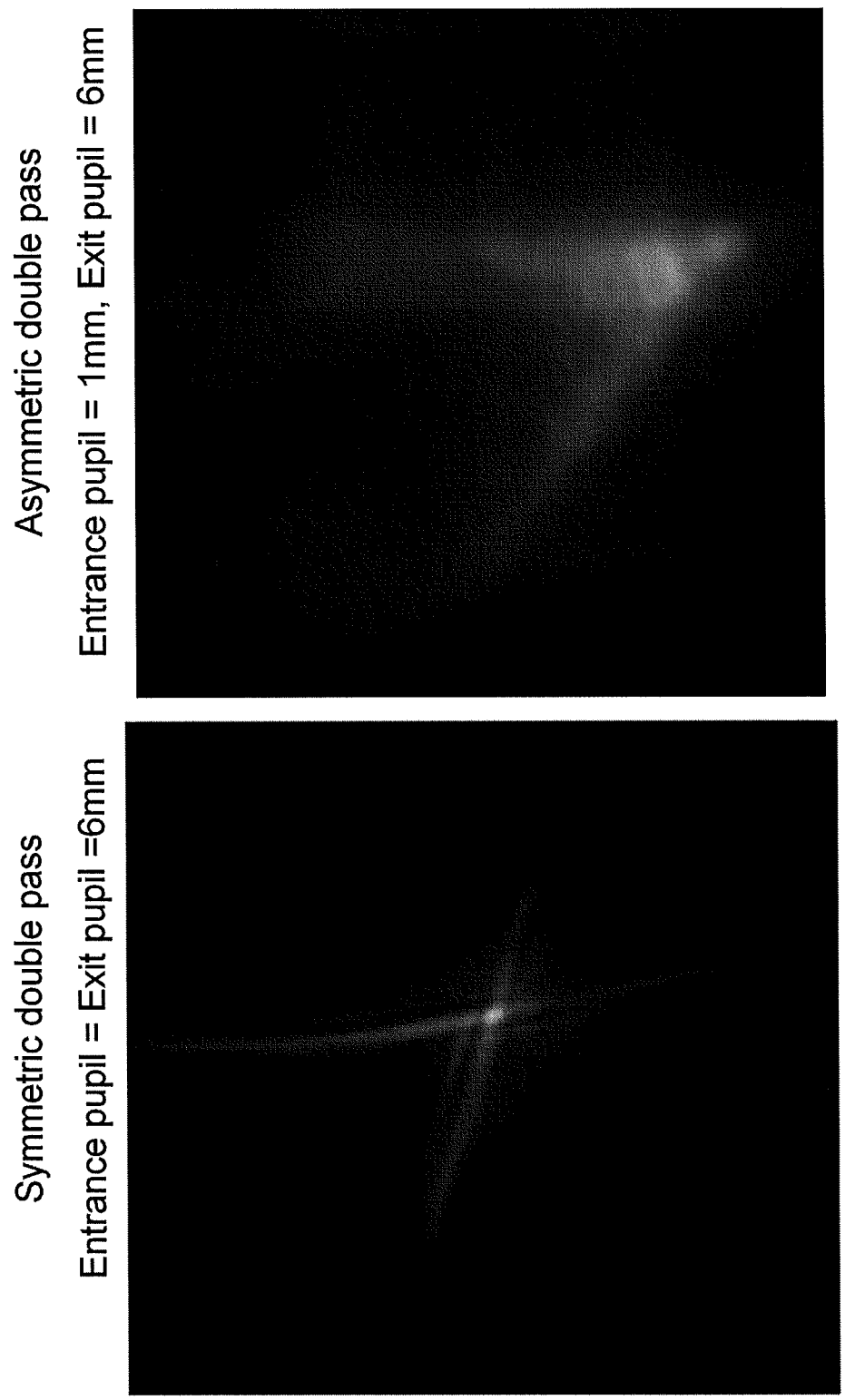
FIGS. 5-7 are photographs that show images from a 2 μm coma phase plate for various techniques.
Figure 6:
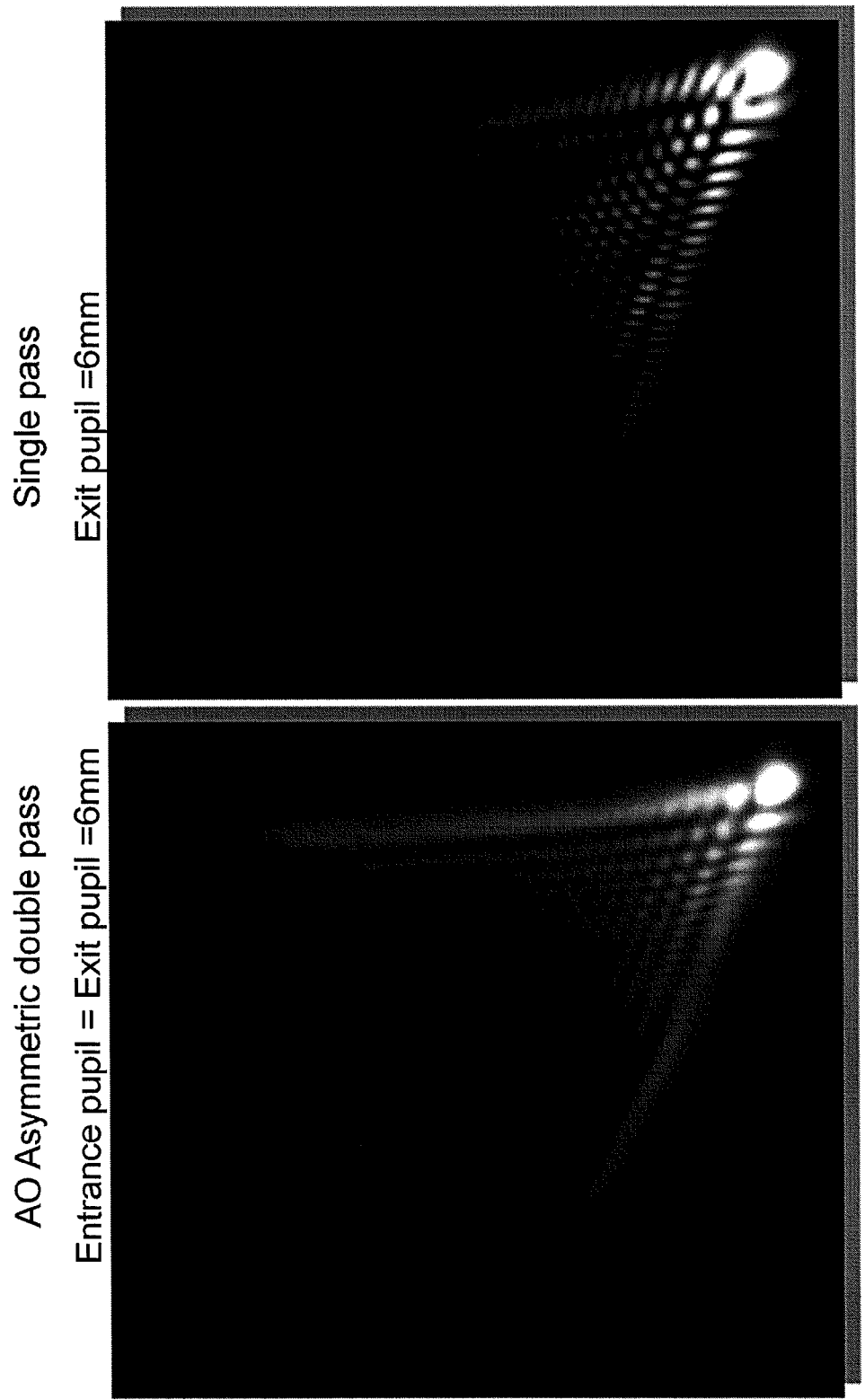
Figure 7:
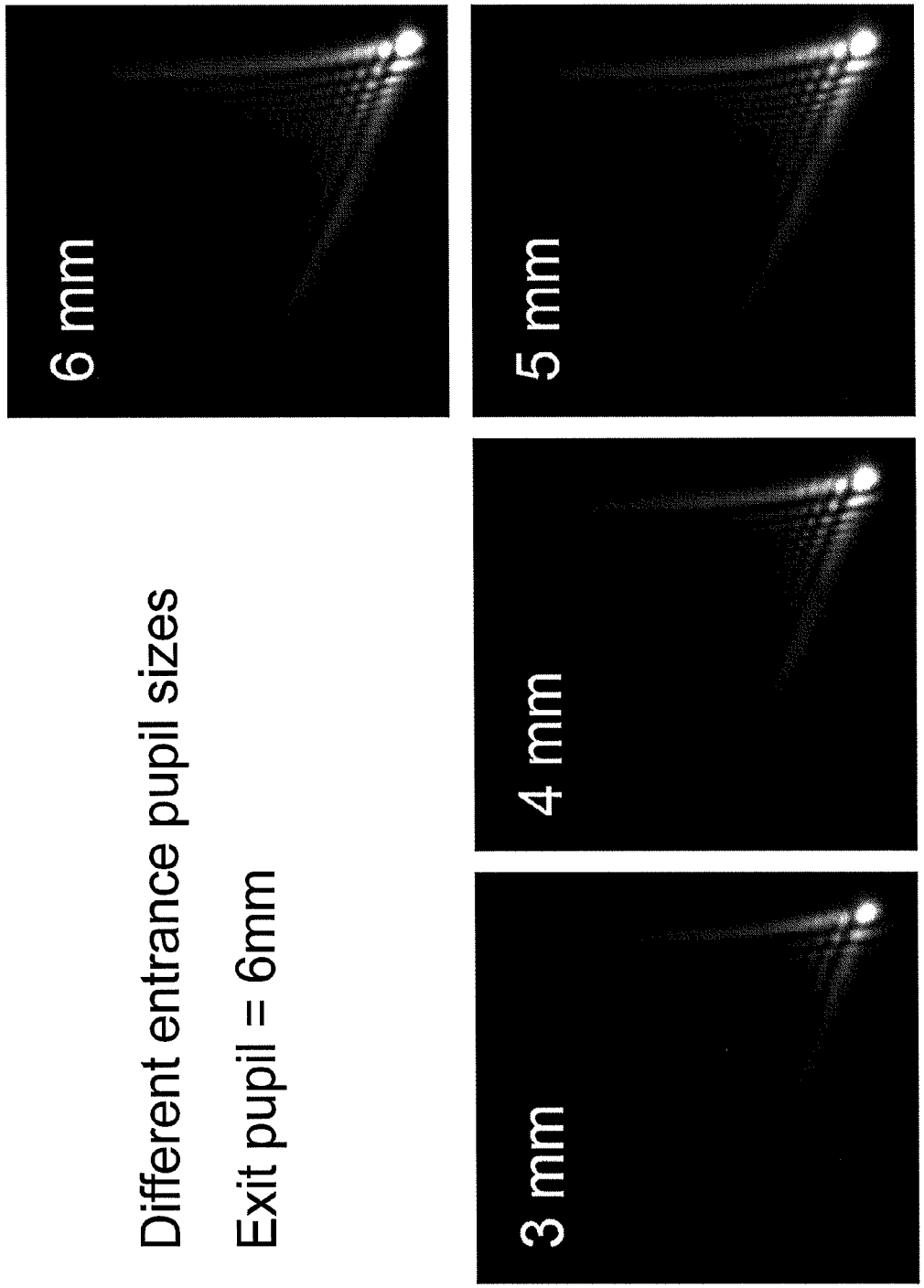
Figure 8:
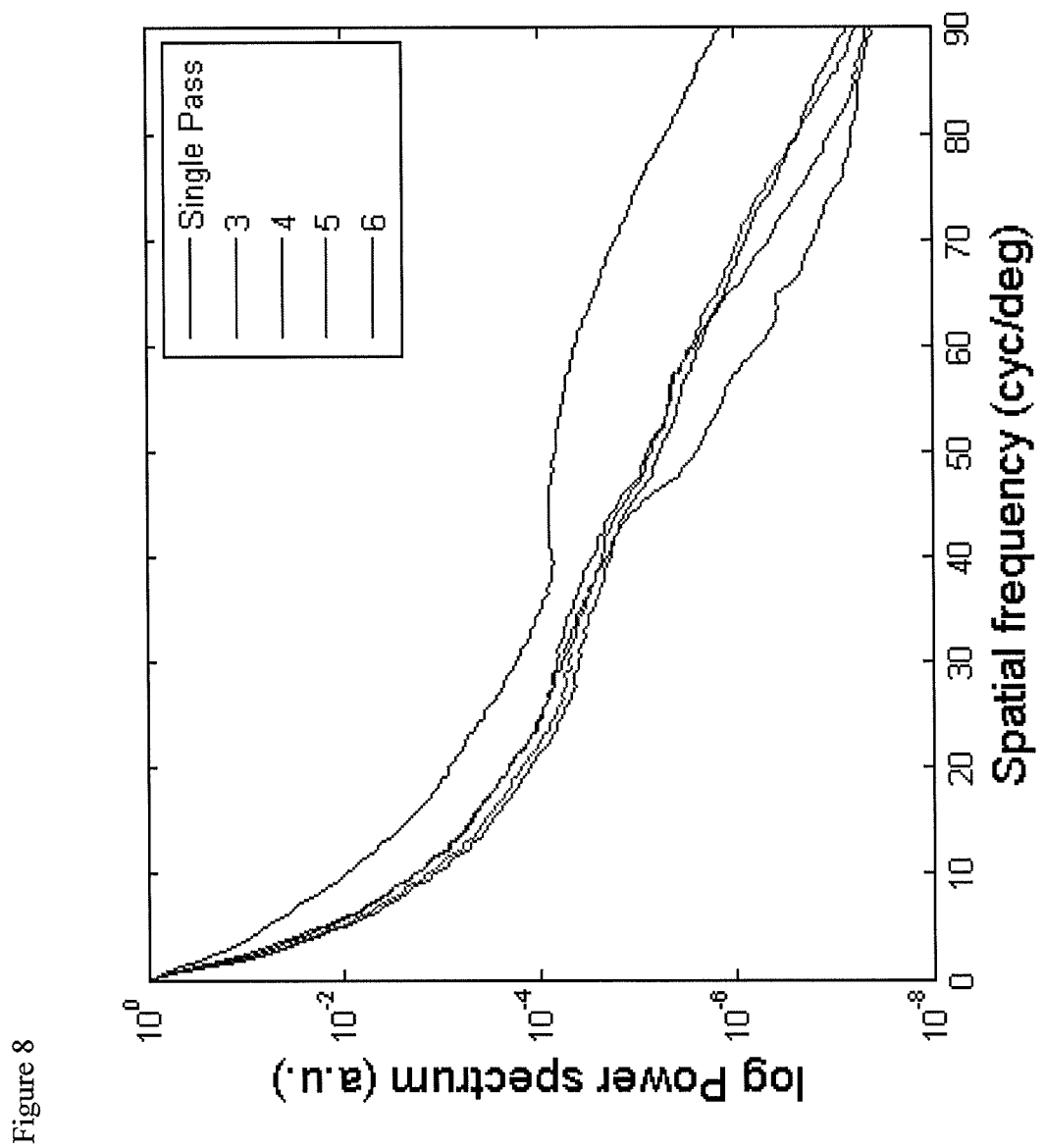
FIG. 8 is a plot that shows plots of power spectrum versus pupil size.
Figure 9A:
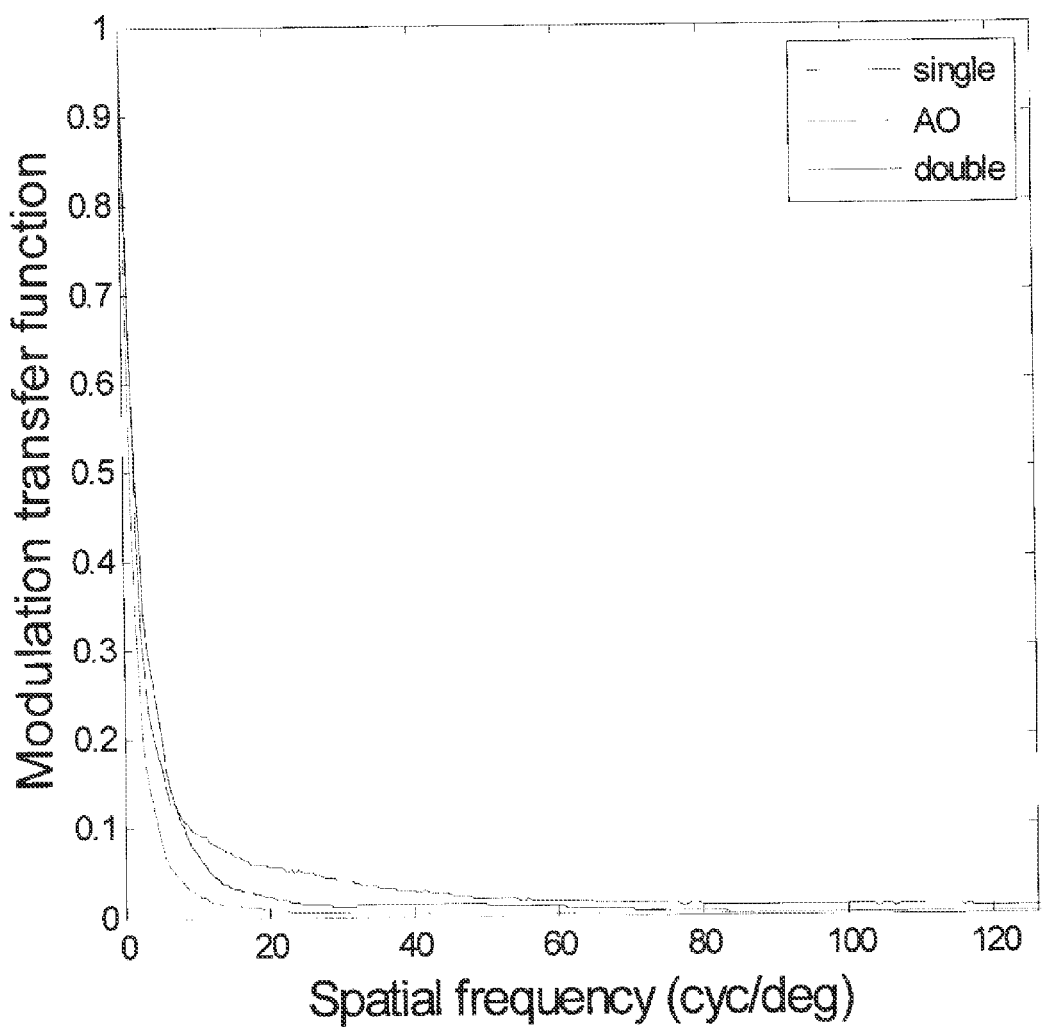
FIGS. 9A and 9B are plots that show the modulation transfer function and its logarithm.
Figure 9B:
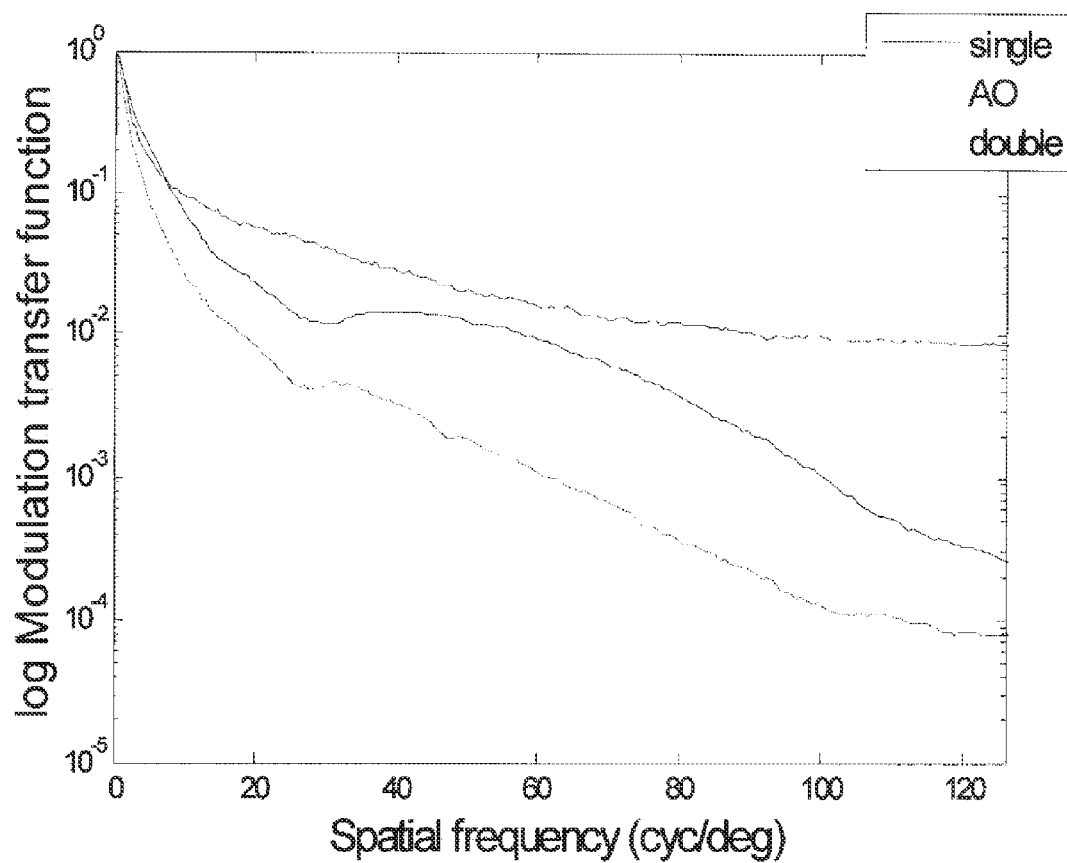
Figure 10:
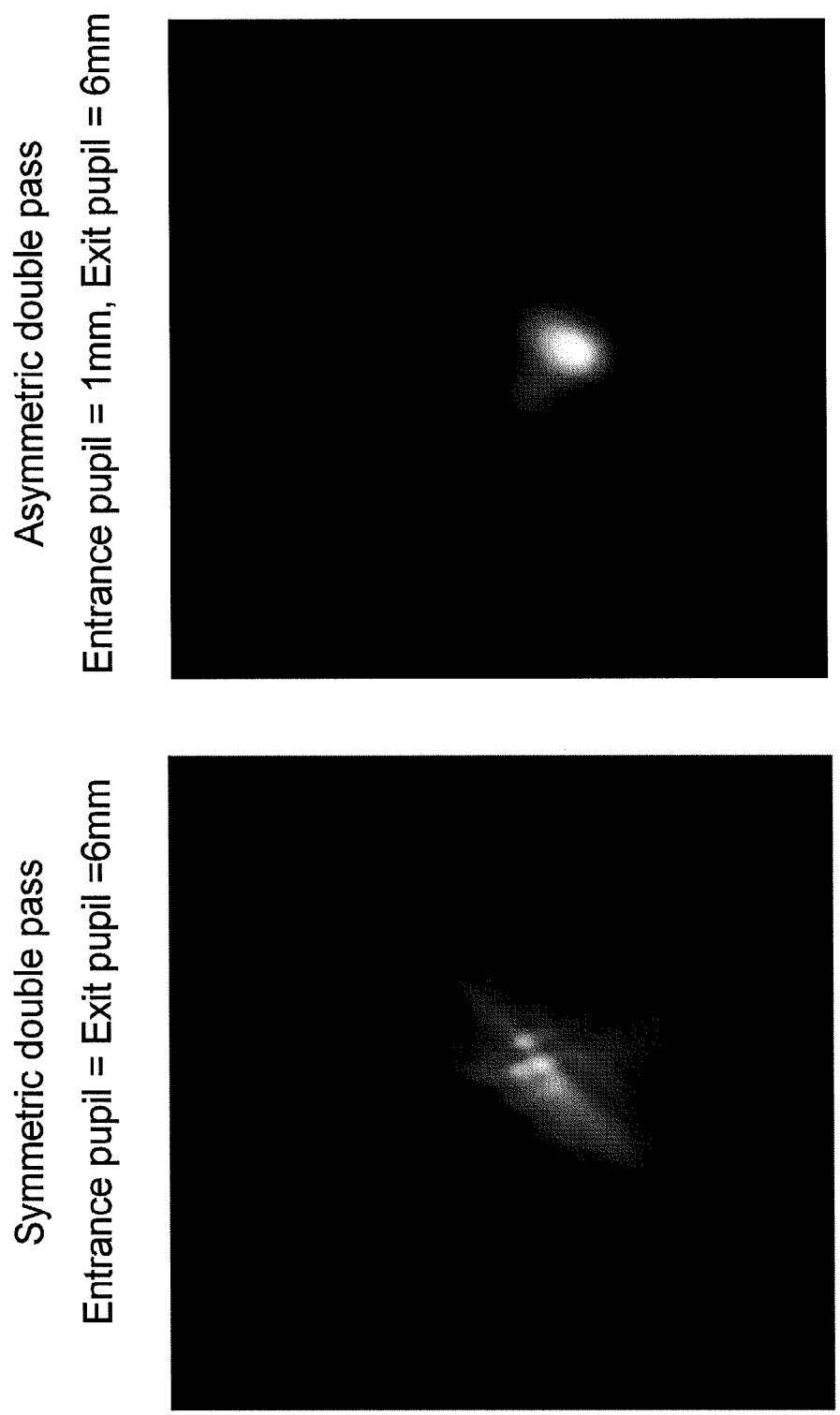
FIGS. 10-14 are photographs and plots that correspond to FIGS. 5-8 and 9A, except for a 0.5 μm coma phase plate.
Figure 11:
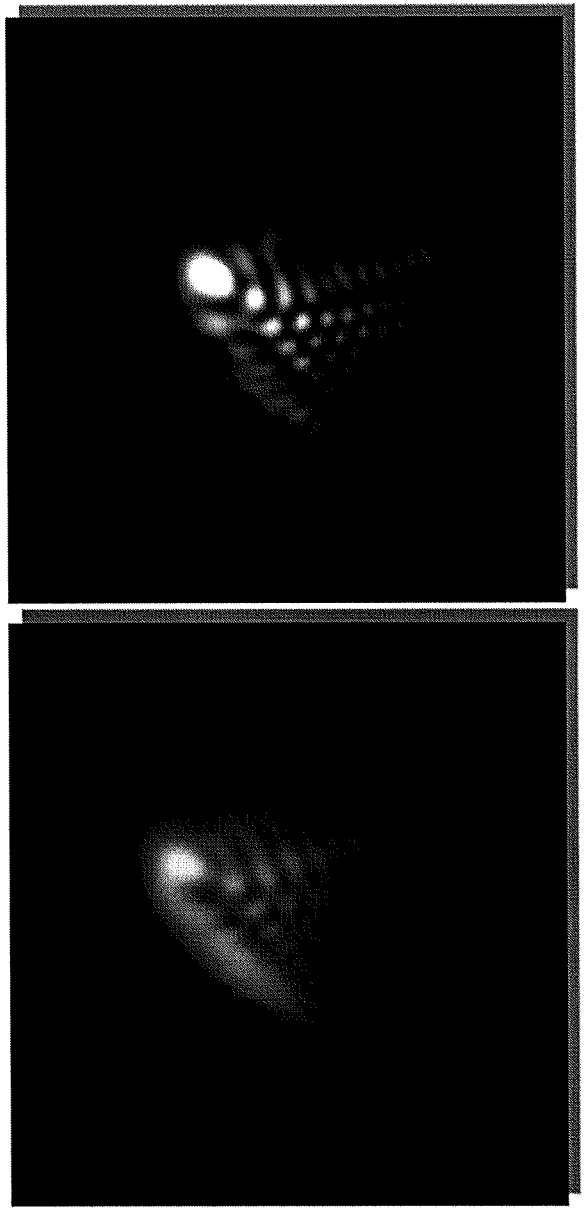
Figure 12:
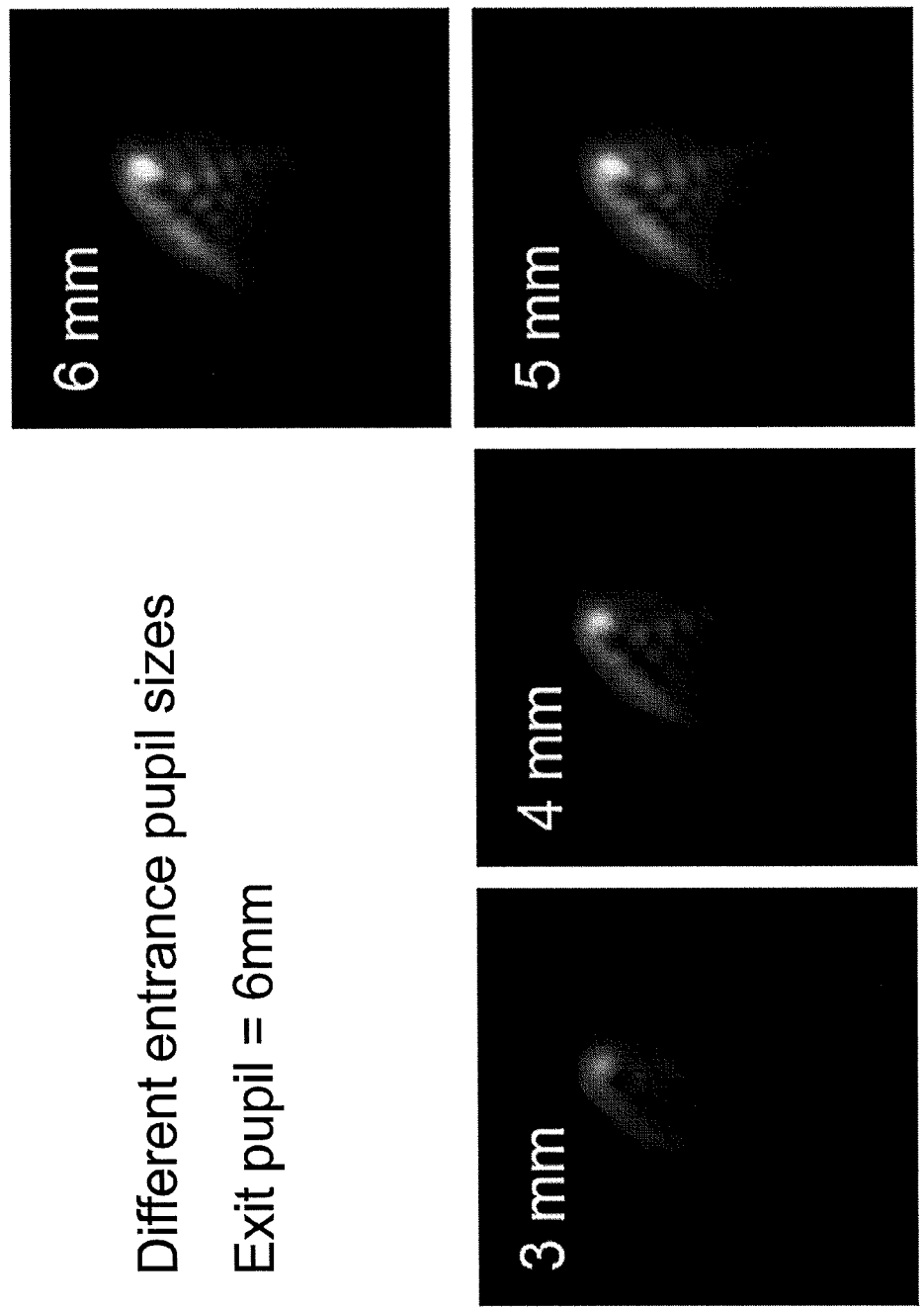
Figure 13:
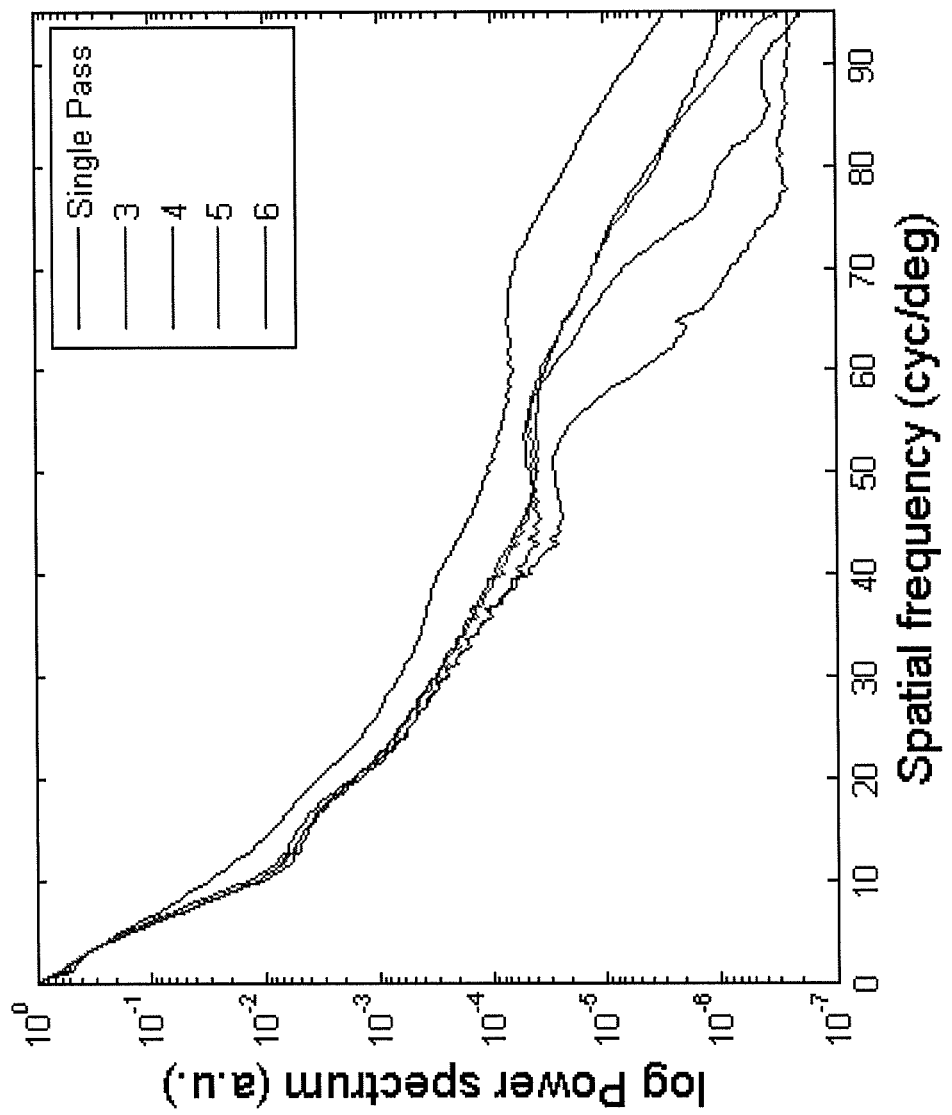
Figure 14:
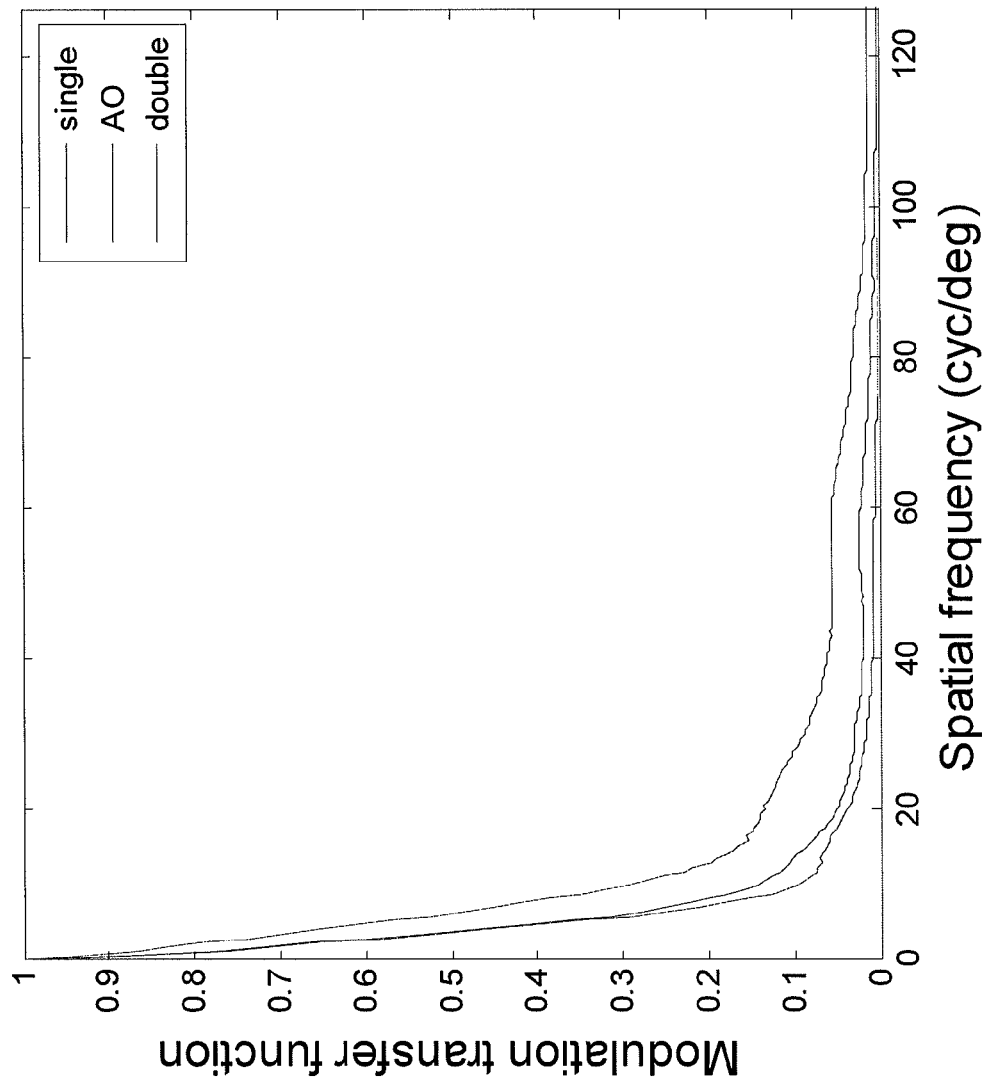

FIG. 5 shows images from a 0.5 μm coma phase plate for symmetric and asymmetric double passes demonstrating the loss of phase information (odd symmetry) and high spatial frequency features respectively. FIG. 6 shows images from the same coma phase plate for an AO asymmetric double pass and the single pass PSF as reference, demonstrating the reliable agreement between the two. FIG. 7 shows images from the same coma phase plate for 3 mm entrance pupil size using the AO asymmetric double pass. Decrease in higher spatial frequencies is noted with a decrease in entrance pupil size. A comparison of the modulation transfer function obtained from all methods is shown in FIG. 8 demonstrating the benefit of the AO asymmetric double pass with 6 mm entrance pupil over others. FIGS. 9A and 9B show the modulation transfer function and its logarithm, respectively, for the symmetric, asymmetric, and AO asymmetric double passes.

FIGS. 10-14 correspond to FIGS. 5-8 and 9A, except for a phase plate derived from a real eye's aberration.

Figure 15:
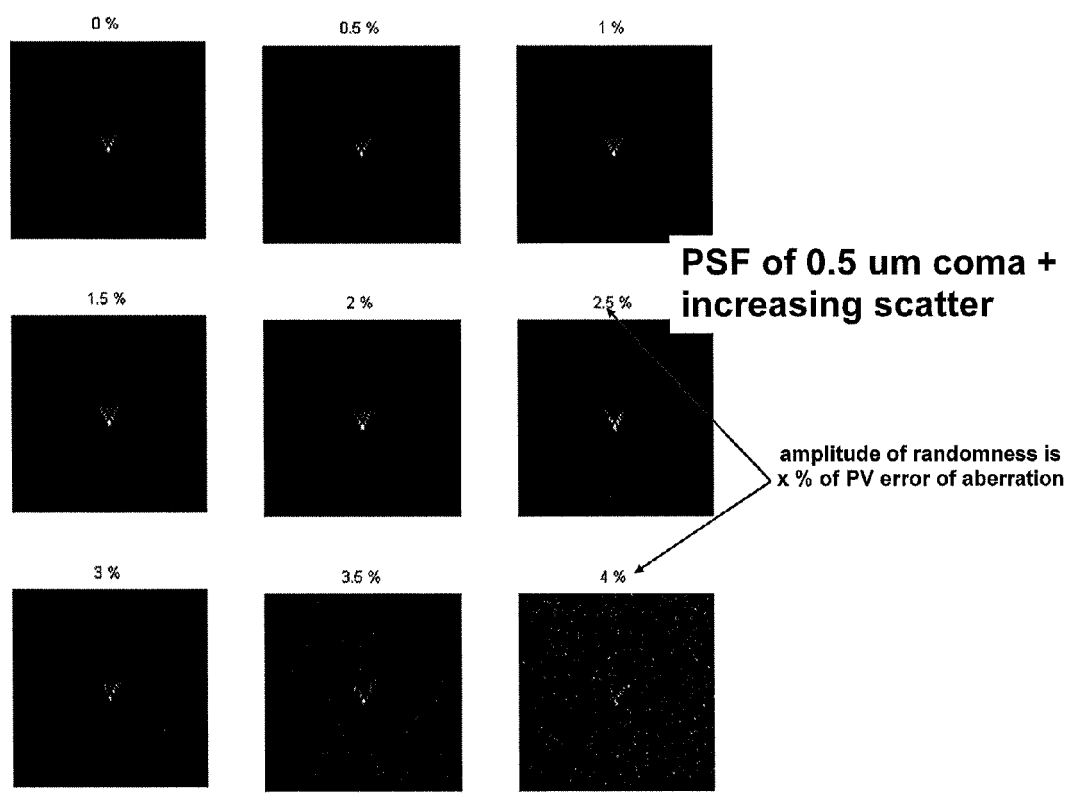
FIG. 15 is a set of photographs that show a point-spread function.
Figure 16:
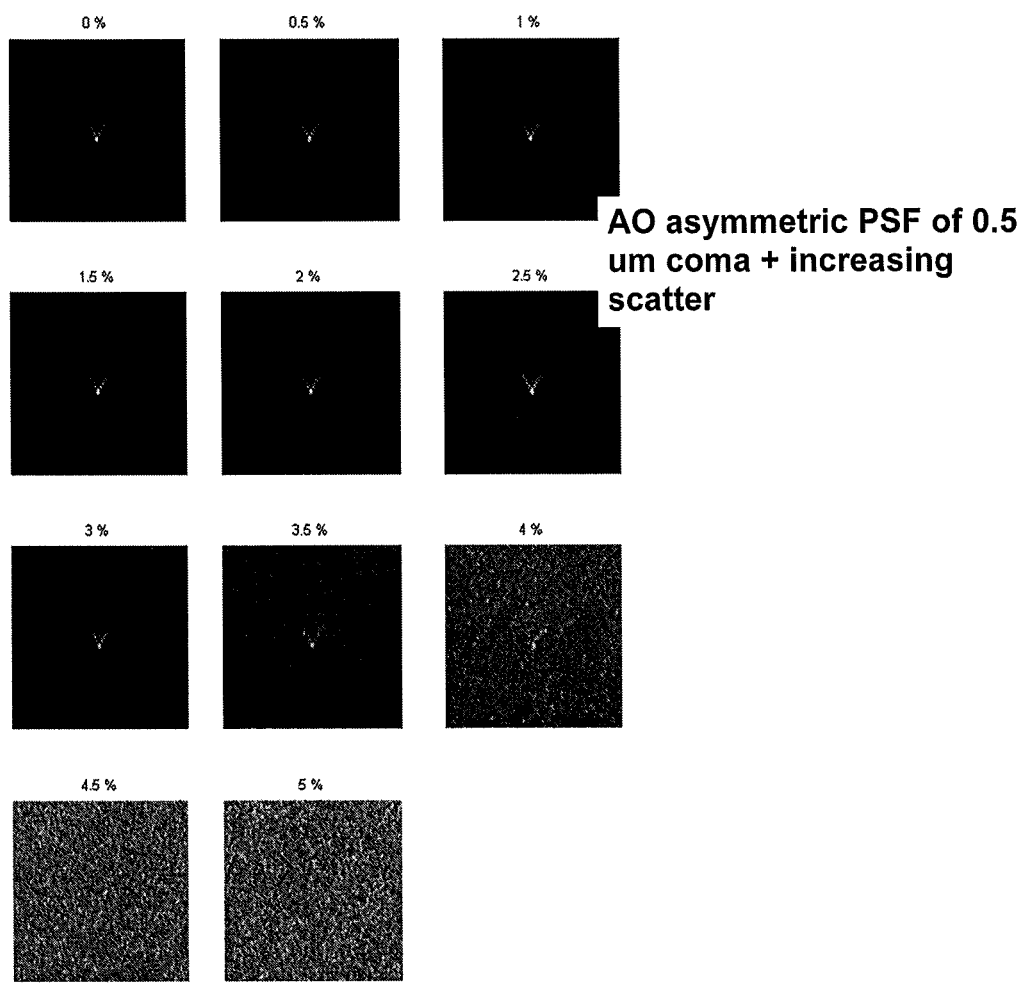
FIG. 16 is a set of photographs that show an asymmetric AO PSF.
Figure 17:
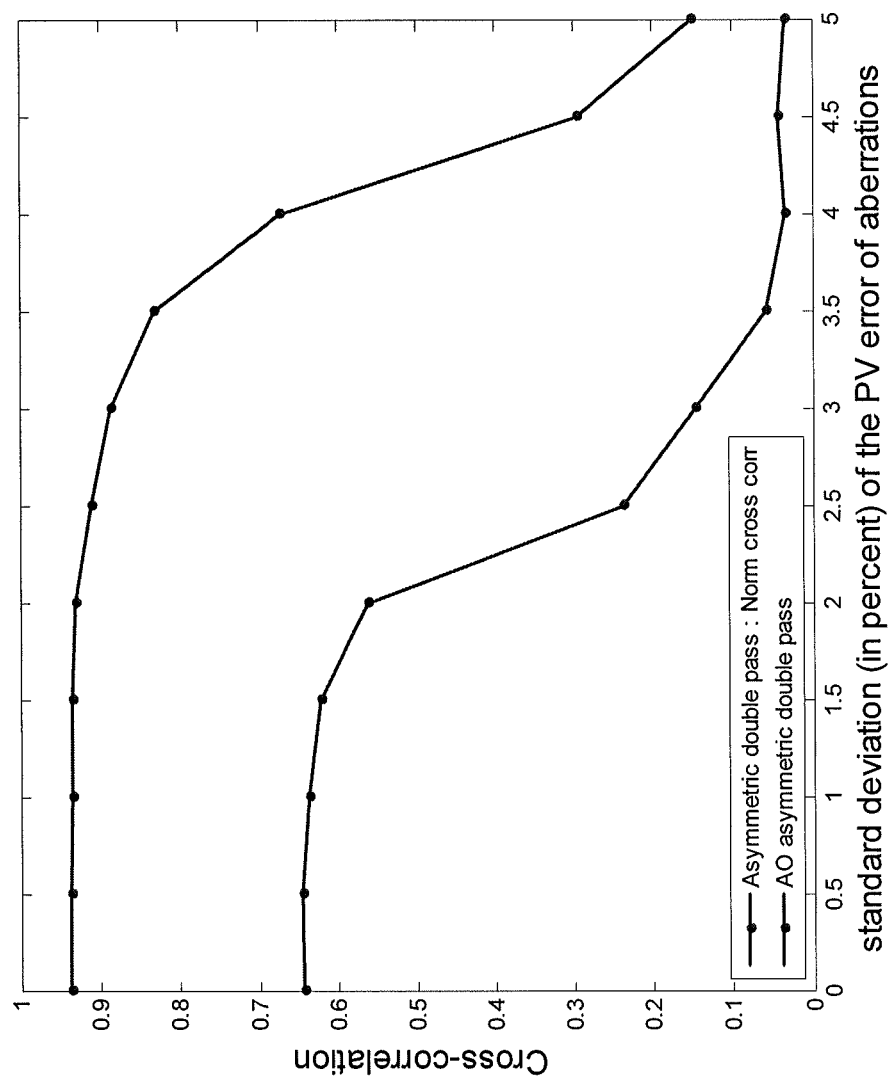
FIG. 17 is a plot that shows the benefit of estimating the PSF with AO.
Figure 18:
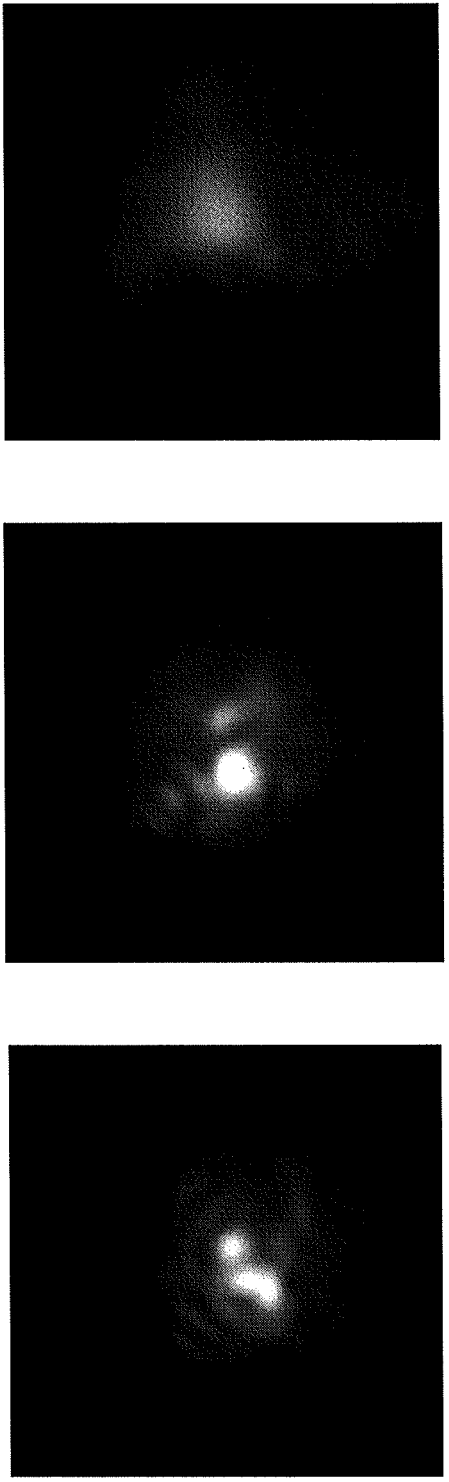
FIG. 18 is a set of photographs that show results from a real eye with three kinds of double pass.
Figure 19:
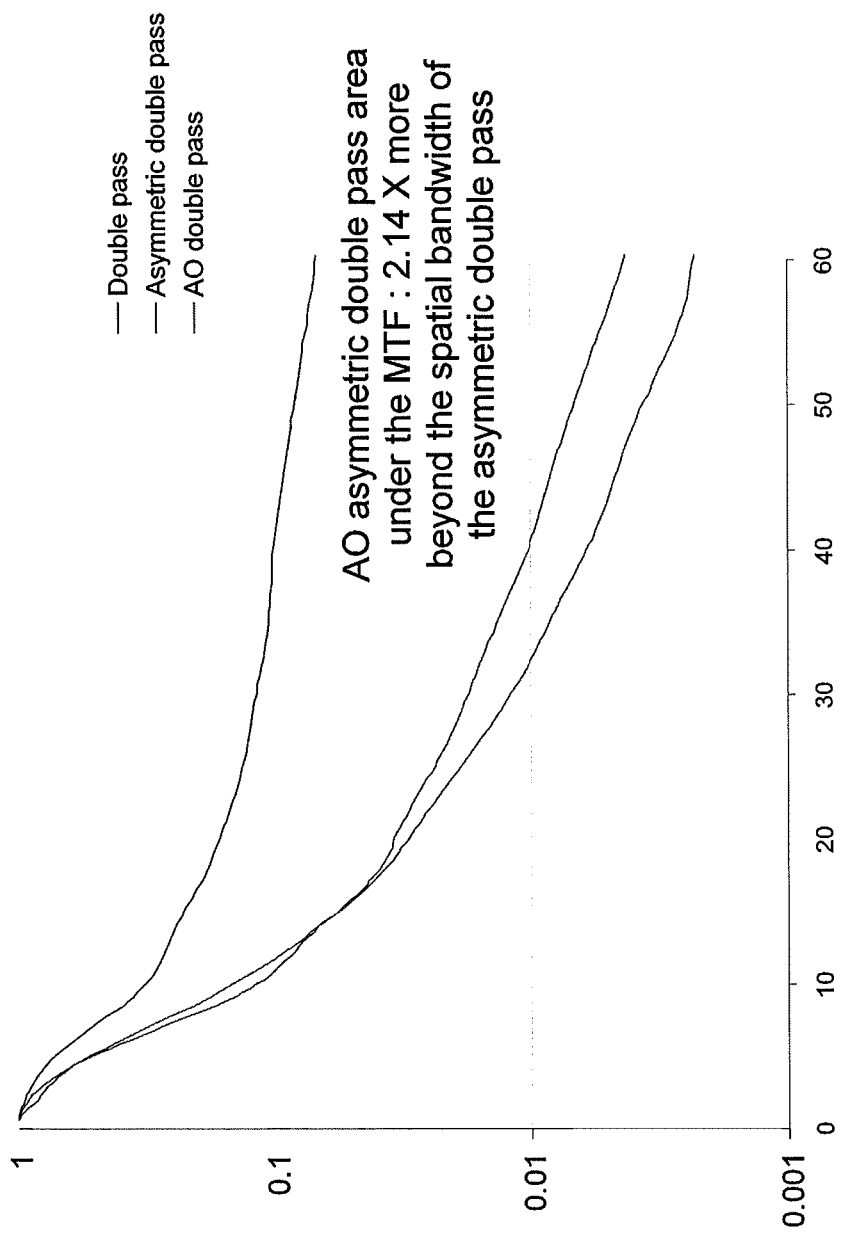
FIG. 19 is a plot that compares the modulation transfer function for the three kinds of double pass.

Traditional wavefront sensing is limited in estimating high frequency defects such as that induced by scatter and tear film dynamics FIG. 15 shows the single pass reference PSF of 0.5 μm coma with increasing scatter. Scatter is represented as the amplitude of randomness given by the percentage of the peak-to-valley error of aberration. FIG. 16 shows the ability of AO asymmetric method to capture the PSF in the same condition of aberration with scatter FIG. 17 shows the benefit of estimating the PSF with AO asymmetric method in the presence of ocular scatter compared to the traditional asymmetric double pass method. As shown, the cross-correlation with the reference single pass PSF is considerably higher with AO asymmetric method than with the traditional asymmetric double pass. FIG. 18 shows results from a real eye with the three double pass methods. The traditional symmetric and asymmetric double passes demonstrate the loss of phase information (odd symmetry) and high spatial frequency features respectively, while the AO asymmetric double pass overcomes both limitations. FIG. 19 shows the corresponding plots of the real eye's modulation transfer function (MTF) with the three methods. As shown, area under the MTF with the AO asymmetric double pass is 2.14 times higher beyond the spatial bandwidth of the asymmetric double pass.

Figure 20:
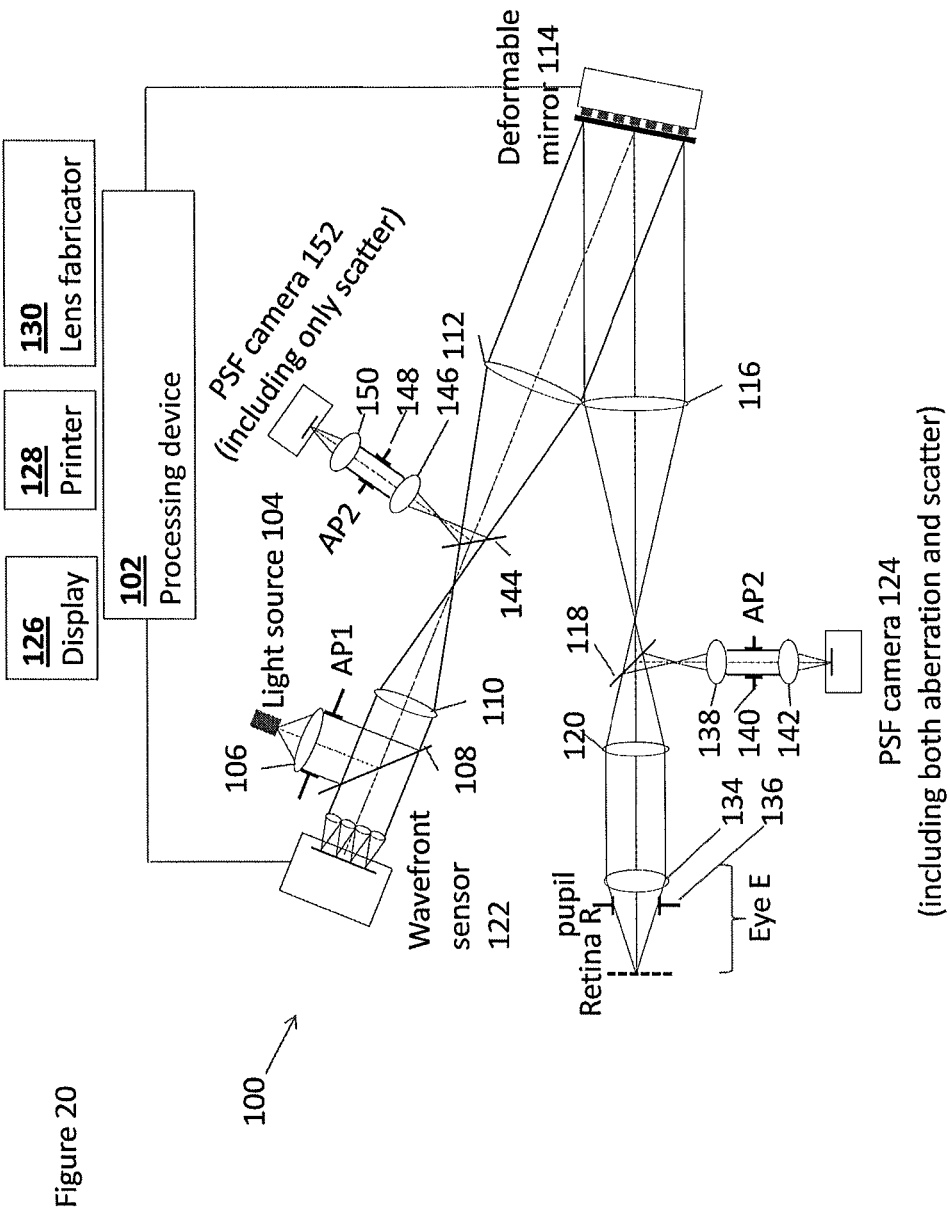
FIG. 20 is a block diagram of a system on which the preferred embodiment can be implemented.

FIG. 20 is a block diagram showing a system 100 on which the preferred embodiment can be implemented. The system operates under the control of a processing device 102 programmed to carry out the operations disclosed herein and in particular to implement closed loop control. Light L from a light source 104 is made incident, through a lens 106 that collimates the light at an aperture 132 having a diameter AP2, a beamsplitter 108, lenses 110 and 112, a deformable mirror or other adaptive optics 114, a lens 116, a beamsplitter 118, a lens 120 that collimates the light, a focusing lens 134, and an artificial pupil 136 at a plane conjugate to the pupil plane, on the retina R of the eye E. Light reflected from the retina R passes through the beamsplitter 108 to a wavefront sensor 122, which supplies detection signals to the processor 102. In the first pass, the processor 102 controls the adaptive optics 114 to focus the light into a tiny spot on the retina R, as described above. In the second pass, light scattered from the tiny spot is picked off by the beamsplitter 118 and focused through a lens 138, an aperture 140 having a diameter AP2, and another lens 142 onto another detector, namely, PSF camera 124, to form the point-spread function, but this time without adaptive optics correction. The PSF formed by the camera 124 includes both aberration and scatter. After the deformable mirror, light is picked off by a beamsplitter 144, and focused by a lens 146, an aperture 148 having a diameter AP2, and a lens 150 onto another PSF camera 152 to form the PSF with scatter only, since the deformable mirror 114 has removed the aberration. The detector images so obtained are processed according to the parameters of the first pass to give the optical PSF. The processor analyzes the detection data to determine the appropriate vision correction and outputs the determination to at least one of a printer 126, a display 128, and a custom lens fabricator 130.

While a preferred embodiment has been set forth above, those skilled in the art who have reviewed the present disclosure will readily appreciate that other embodiments can be realized within the scope of the invention. For example, any suitable AO methodology can be used. Therefore, the present invention should be construed as limited only by the appended claims.

We claim:

1. A method for measuring an optical point spread function (PSF) of a patient's eye, the method comprising:
   (a) detecting wavefront aberrations in the eye, using a detector;
   (b) performing a first pass using a large pupil size, the first pass comprising:
      (i) determining an appropriate correction to be applied to a wavefront correcting device that uses adaptive optics; and
      (ii) focusing light from a light source into a point source on the retina of the patient's eye by controlling the wavefront correcting device in accordance with the wavefront aberrations detected in step (a) and the appropriate correction determined in step (b)(i);
   (c) performing a second pass using a second pupil size that is larger than or equal to the first pupil size, the second pass comprising:
      (i) splitting the light reflected from the retina before the adaptive optics to capture the PSF with effects from aberration and scatter; and
      (ii) splitting the light reflected from the retina after the adaptive optics to capture the PSF with the aberration corrected by the adaptive optics;
   (d) deriving the optical PSF of the eye from PSF captured in steps (c)(i) and (c)(ii); and
   e) computing the optical transfer function comprising modulation and phase transfer functions from the optical PSF in step (d).

2. The method of claim 1, wherein steps (d) and (e) are performed automatically.

3. The method of claim 2, further comprising automatically determining corrective optics for the patient's eye in accordance with the optical point spread function.

4. The method of claim 3, further comprising controlling a lens fabrication device to fabricate the corrective optics.

5. The method of claim 1, wherein each of steps (b) and (c) comprises pupil size control by having an artificial pupil at the pupil conjugate.

6. A system for measuring an optical point spread function of a patient's eye, the system comprising:
   a light source;
   a wavefront correcting device using adaptive optics for causing light from the light source to be incident on the retina of the patient's eye;
   a detector for detecting the light once the light has been reflected from the retina; and
   a processing device in communication with the adaptive optics and the detector, the processing device being configured for:
   (a) detecting wavefront aberrations in the eye, using the detector;
   (b) performing a first pass using a large pupil size, the first pass comprising:
      (i) determining an appropriate correction to be applied to the adaptive optics; and
      (ii) focusing light from a light source into a point source on the retina of the patient's eye by controlling the wavefront correcting device in accordance with the wavefront aberrations detected in step (a) and the appropriate correction determined in step (b)(i);
   (c) performing a second pass using a second pupil size that is larger than or equal to the first pupil size, the second pass comprising:
      (i) splitting the light reflected from the retina before the adaptive optics to capture the PSF with effects from aberration and scatter; and
      (ii) splitting the light reflected from the retina after the adaptive optics to capture the PSF with the aberration corrected by the adaptive optics;
   (d) deriving the optical PSF of the eye from PSF captured in steps (c)(i) and (c)(ii); and
   e) computing the optical transfer function comprising modulation and phase transfer functions from the optical PSF in step (d).

7. The system of claim 6, further comprising an output, in communication with the processor, for outputting the optical point spread function.

8. The system of claim 7, wherein the processor is configured to perform steps (d) and (e) automatically.

9. The system of claim 8, wherein the processor is further configured for automatically determining corrective optics for the patient's eye in accordance with the optical point spread function.

10. The system of claim 9, wherein the output comprises a lens fabrication device for fabricating the corrective optics.

11. The system of claim 6, further comprising an artificial pupil for placement at the pupil conjugate, and wherein the system is configured such that each of steps (b) and (c) comprises pupil size control by having the artificial pupil at the pupil conjugate.

\* \* \* \* \*